(12) United States Patent
Cleary (10) Patent No.: US 7,053,373 B1
(45) Date of Patent: May 30, 2006

(54) INFRARED SPECTROMETER WITH AUTOMATED TABLET SAMPLING

(75) Inventor: Joseph A. Cleary, Dodgeville, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 5 days.

(21) Appl. No.: 11/040,350

(22) Filed: Jan. 19, 2005

(51) Int. Cl.
*G01N 35/02* (2006.01)
*G01N 33/15* (2006.01)

(52) U.S. Cl. .............................. 250/339.07; 250/339.08

(58) Field of Classification Search ........... 250/339.07, 250/339.08, 339.09; 356/451, 452, 455, 356/456
See application file for complete search history.

(56) References Cited

U.S. PATENT DOCUMENTS

| | | | |
|---|---|---|---|
| 4,234,538 A * | 11/1980 | Ginsberg et al. | 422/64 |
| 4,259,289 A * | 3/1981 | Curry et al. | 422/64 |
| 4,415,811 A | 11/1983 | Beck et al. | |
| 4,641,534 A * | 2/1987 | Schneider et al. | 73/856 |
| 4,695,727 A | 9/1987 | Brierley et al. | |
| 4,882,493 A | 11/1989 | Lodder et al. | |
| 5,094,786 A * | 3/1992 | Nagashima et al. | 264/411 |
| 5,214,277 A | 5/1993 | Drennen, III | |
| 5,227,856 A | 7/1993 | Reed et al. | |
| 5,340,747 A | 8/1994 | Eden | |
| 5,679,954 A * | 10/1997 | Soloman | 250/339.08 |
| 5,760,399 A | 6/1998 | Trygstad | |
| 5,764,355 A * | 6/1998 | Gagnon et al. | 356/244 |
| 6,014,212 A * | 1/2000 | Hammond et al. | 356/319 |
| 6,375,898 B1 * | 4/2002 | Ulrich | 422/64 |
| 6,644,136 B1 | 11/2003 | Carney et al. | |
| 6,667,808 B1 | 12/2003 | Clermont et al. | |
| 2003/0022380 A1 * | 1/2003 | Jakubowicz et al. | 436/54 |

OTHER PUBLICATIONS

Nicolet Antaris Near-IR Analyzers—Method Transferability through Superior Engineering, Thermo Electron Corporation, 2003.
Industrial Analyzers, Thermo Electron Corporation, 2004, pp. 98-99.
Automation Tools for the Nicolet Antaris FT-NIR Analyzer, Thermo Electron Corporation, 2004.
Antaris Near-IR Analyzer user manual, Thermo Nicolet Corporation, 2002, pp. 33-34, 43-44.

* cited by examiner

*Primary Examiner*—David Porta
*Assistant Examiner*—Mark R. Gaworecki
(74) *Attorney, Agent, or Firm*—Foley & Lardner LLP; Charles B. Katz (57) ABSTRACT

An infrared spectrometer system with automated tablet sampling includes an infrared spectrometer providing a modulated output beam to a sample position, and reflected and transmitted light detectors. A tablet holding wheel is mounted to advance multiple tablets one at a time to the sample position. The tablet holding wheel includes a tablet wheel base having a plurality of transmission openings therein in a circular pattern around a central axis of the base, grippers adjacent to each of the transmission openings that are movable inwardly and outwardly, and a cam ring mounted to and rotatable with respect to the tablet wheel base, the cam ring being operatively engaged with the grippers to move the grippers outwardly and inwardly to engage and hold tablets over the transmission openings. The tablet holding wheel can be automatically rotated to move a tablet to the sample position where analysis can be carried out, to advance the tablet wheel to move the next tablet into position for analysis, and to repeat the process until all of the tablets have been analyzed.

29 Claims, 6 Drawing Sheets

INFRARED SPECTROMETER WITH AUTOMATED TABLET SAMPLING

FIELD OF THE INVENTION

This invention pertains generally to the field of Fourier transform infrared spectrometers and to sample holders for such spectrometers.

BACKGROUND OF THE INVENTION

Fourier transform infrared (FTIR) spectrometers are utilized to perform accurate and efficient identification of the chemical composition of a sample. Such spectrometers typically incorporate a Michelson interferometer having a moving mirror. The interferometer modulates the infrared beam from an infrared source to provide an output beam in which the intensity of the infrared radiation at various wavelengths is periodically varied. The output beam is focused and passed through or reflected from a sample, after which the beam is collected and focused onto a detector. The detector provides a time varying output signal which contains information concerning the wavelengths of infrared absorbance or reflectance of the sample. Fourier analysis is then performed on the output signal data to yield usable information on the chemical composition of the sample.

Conventional FTIR spectrometers include a sample chamber in which a sample is held in a position to be exposed to the infrared beam from the spectrometer. The sample which is to be analyzed may take various physical states, i.e., a liquid, solid or gas, and solid samples may have various physical characteristics. For example, a solid material to be analyzed may be in the form of a block or sheet of material (e.g., polymer plastics), in the form of powders or granulates, or in specific formed shapes (e.g., pharmaceutical pills and capsules). An example of a infrared spectrometer system that can be utilized to carry out analysis of pharmaceutical samples in both the reflectance mode and the transmission mode is shown in U.S. Pat. No. 6,667,808, entitled Multifunctional Fourier Transform Infrared Spectrometer System.

Pharmaceutical tablets may take various shapes and sizes. Typically, an operator will test one tablet at a time by placing the tablet in a sample position where it is usually engaged with a holder or variable aperture which locates the tablet in the proper sample position and which also minimizes the infrared light transmitted around the tablet. Where a large number of tablets are to be sampled, a significant amount of operator time is required to remove each tablet and replace it with another tablet in the proper position for sampling, and to attend to the spectrometer while the analysis is carried out. Tablet holding wheels or turntables have been used to allow several tablets to be deposited by the operator at one time on the wheel, which is then automatically advanced to bring one of the tablets at a time into the sample position for analysis. However, when sampling of one batch of tablets of a particular size and shape is completed, and sampling of a new batch of tablets of a different size and shape is to be carried out, a new specialized holder is generally required to accommodate the size and shape of the new batch of tablets to be analyzed.

SUMMARY OF THE INVENTION

An infrared spectrometer system in accordance with the present invention is capable of automated analysis of multiple tablets or other solid samples with minimal operator intervention. Samples are held in a tablet holding wheel system at a sample position in a manner which allows analysis of the sample in both reflection of infrared light from the sample and transmission of infrared light through the sample.

In the present invention, an infrared spectrometer may be utilized which provides a modulated output beam on a beam path. Optical elements transmit the modulated output beam from the spectrometer toward a sample position. A reflected light infrared detector detects infrared light that is reflected from a sample at the sample position, and a transmitted light infrared detector is mounted adjacent to the sample position to receive infrared light passed through a sample held in the sample position. A tablet holding wheel is mounted to advance multiple tablets one at a time to the sample position. The tablet holding wheel includes a tablet wheel base having a plurality of transmission openings therein arranged in a circular pattern around a central axis of the base, wherein the base is rotatable about its central axis. Grippers adjacent to each of the transmission openings are movable inwardly and outwardly over the transmission openings. The grippers when moved inwardly can engage and hold a tablet in its proper position over each transmission opening. A cam ring is mounted to the tablet wheel base and is rotatable with respect to the base about the central axis in two opposite directions. The cam ring is operatively engaged with the grippers to move the grippers outwardly in one direction of rotation of the cam ring and to move the grippers inwardly in the other direction of rotation of the cam ring.

In using the present invention, the operator places a tablet in one or more of the tablet holding positions in the wheel and then moves the cam ring to cause the grippers to firmly engage the tablet. Preferably, the operator uses one tablet to size the grippers to fit the tablet. The operator then secures the cam ring in this position and places tablets at some or all of the other tablet holding positions. The operator can then operate the spectrometer to begin analyzing the tablets held within the tablet wheel. The spectrometer automatically advances the tablet wheel using a drive motor to bring a tablet into the sample position, carry out spectrographic analysis on the sample tablet, move the tablet wheel to the next position, and repeat the process until all of the tablets have been analyzed. The operator may then remove the tablets that have been analyzed, and another set of tablets of the same size and shape may then be inserted in the tablet holding positions. The cam ring does not need to be adjusted until a new tablet of different size and shape is to be analyzed. Because the grippers adapt to different shapes and sizes of tablets, no replacement or adjustment of the tablet wheel is required between batches of tablets having different shapes and sizes.

The grippers may comprise two gripping arms mounted for rotation about a pivot point adjacent to each transmission opening in the base, with each arm having a gripping head shaped to engage a portion of a tablet at one end of the arm and a cam pin extending from the opposite end of the arm from the gripping head. The arms are pivotally connected to the base at a central position of each arm between the gripping head and the cam pin. The cam ring has a plurality of openings therein that are aligned with each of the openings in the base and which enclose the gripping heads of the gripping arms to permit movement of the gripping heads inwardly and outwardly within the openings in the cam ring. The cam ring further can include slots for each of the cam pins of the gripping arms, with each cam pin of each gripping arm inserted and slidable within a slot in the cam ring. The slots are oriented such that rotation of the cam ring in one of its directions of motion drives the cam pins to rotate the gripping heads of the gripping arms inwardly, and such that the slots engage the cam pins to rotate the gripping heads of the gripping arms outwardly when the cam ring is rotated in its opposite direction of rotation. The gripping heads are preferably formed to have a portion extending upwardly through the openings in the cam ring and above a ledge formed by adjacent portions of each gripping arm. The upwardly extending portions of the gripping heads preferably have a curved inwardly facing surface suited to engage a curved surface of a tablet. A cover plate may be mounted to the base over the cam ring to cover the cam ring as it slides within the channel of the base. The cover plate has openings therein aligned with the openings in the cam ring and the transmission openings in the base, and preferably has depressed wells therein around each opening in the cover plate. The depressed openings are formed to admit a section of a detector head to better receive the light transmitted through the tablet at the sample position and to minimize interference from stray light.

Further objects, features and advantages of the invention will be apparent from the following detailed description when taken in conjunction with the accompanying drawings.

DETAILED DESCRIPTION OF THE INVENTION

Figure 1:
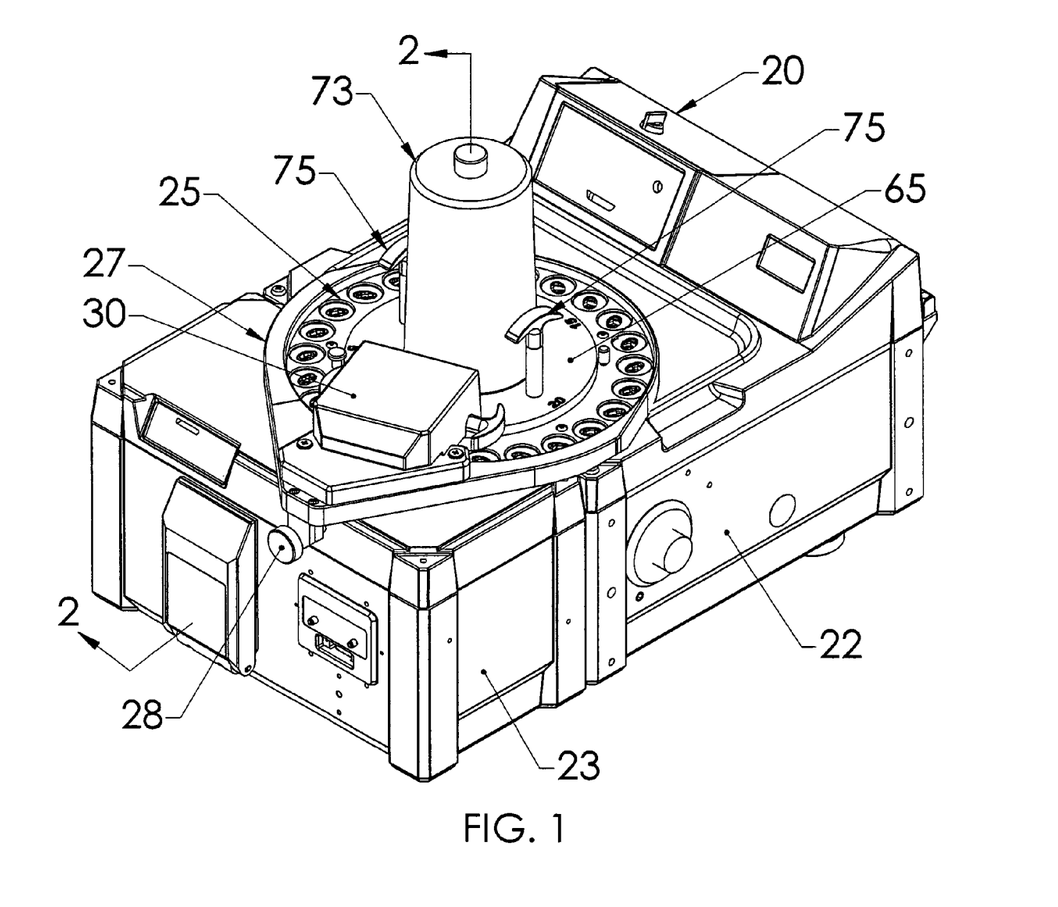
FIG. 1 is a perspective view of an infrared spectrometer system with automated tablet sampling in accordance with the invention.

With reference to the drawings, a spectrometer system with automated tablet sampling is shown generally at 20 in FIG. 1. The system 20 includes an FTIR spectrometer 22, which conventionally includes an infrared source, an interferometer, and various optical elements for filtering and defining the infrared beam as well as signal processing and control electronics, a sample compartment 23 which is shown connected to the spectrometer 22 but which may be incorporated as part of the spectrometer 22, and a tablet holding wheel 25. The tablet holding wheel 25 is mounted to the housings of the spectrometer elements 22 and 23 by a mounting fixture 27 which is detachably connected to the spectrometer housing, for example, using a hand screw connector 28 as shown in FIG. 1 for illustration. A transmission detector unit 30 is mounted above the tablet wheel to receive infrared light passed through a tablet and is connected to provide signals to the spectrometer 22 for analysis of the detected transmitted infrared beam. The spectrometer 22, and the sample compartment 23 forming part of the spectrometer system, may be conventional commercial products which provide a modulated infrared beam that can be used to analyze the tablet samples held in the tablet holding wheel system 25. A preferred spectrometer system is shown in U.S. Pat. No. 6,667,808, issued Dec. 23, 2003, entitled Multifunctional Fourier Transform Infrared Spectrometer System, the disclosure of which is incorporated herein by reference. The present invention will be described for exemplification with respect to such a system; however, it is understood that any other infrared spectrometer system which provides an appropriate modulated infrared beam may be utilized in the present invention.

Figure 2:
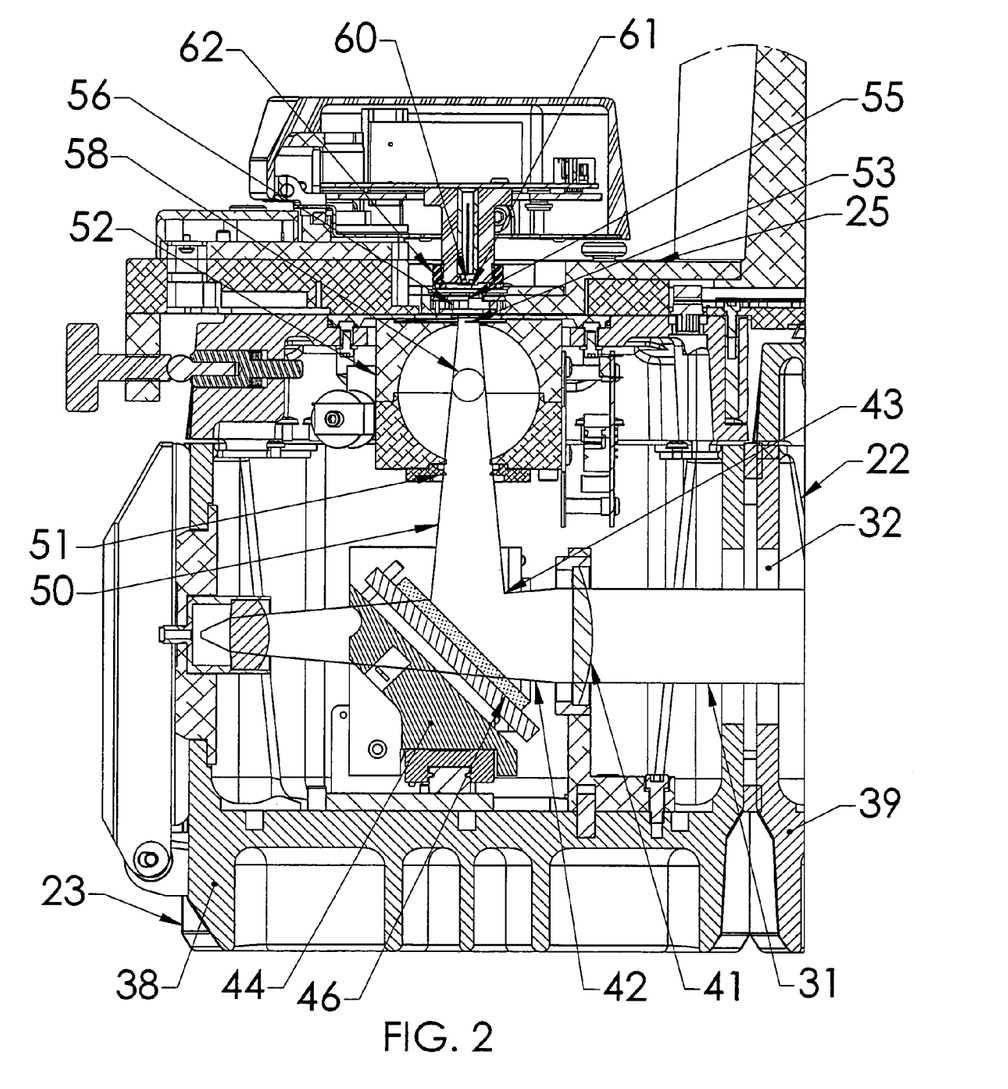
FIG. 2 is a partial cross-sectional view of the system of FIG. 1 taken generally along the lines 2—2 of FIG. 1.

A cross-sectional view through the sample compartment 23, generally illustrating the optical beam path components therein, is shown in FIG. 2. The spectrometer 22 provides an output beam 31 of infrared light that is periodically modulated to provide the appropriate sampling beam for the infrared spectrometer. After exiting through an outlet opening 32, the beam 31 passes on a main beam path into a sample compartment enclosure 38. Although a separate sample compartment enclosure 38 and spectrometer enclosure 39 are illustrated, it is understood that a single enclosure may be utilized. In the enclosure 38 the beam 31 is received by a focusing lens 41 which provides a converging beam 42 that is directed on the main beam path toward a junction position 43. It is understood that focusing mirrors may be used rather than lenses, and that any desired transmissive or reflective optical elements may be used to form the beam path. A multi-position mirror element 44 is mounted for translation toward and away from the position 43 and includes an upwardly diverting mirror 46. The mirror element 44 may have two and preferably three positions, with additional mirrors, as described in U.S. Pat. No. 6,667,808. Alternatively, the mirror element 44 may be fixed in the position in which the upwardly deflecting mirror 46 is interposed into the main beam path converging beam 42 at the junction position 43. The converging beam 42 intercepted by the mirror 46 is deflected upwardly on a beam path into a converging beam 50 that passes through an inlet opening 51 of an integrating sphere 52 and thence through an outlet opening 53 of the integrating sphere to a sample position 55 at which a sample (e.g., a pharmaceutical pill, tablet, capsule, etc., all referred to generally as a "tablet" herein) is held by grippers 56 of the tablet wheel 25. Incident light that is reflected from the sample at the sample position 55 is diffusely reflected from the surfaces of the integrating sphere 52 until incident upon an infrared detector 58 mounted in the sphere 52 which detects the reflected light in the sphere from the sample. Generally, the sample will not be entirely opaque to the light of the incoming beam 50, and a portion will pass therethrough in transmission and will be incident upon a transmitted light detector 60. An aperture element 61 is preferably mounted adjacent to the detector 60 or forms a part thereof to restrict the spatial aperture of the light transmitted through a sample at the sample position 55 in the beam passed to the detector 60, and thereby minimize the incidence of stray light onto the detector 60. The aperture element 61 may comprise a rubber or elastic diaphragm with a central opening smaller than the expected tablet size. The aperture element is positioned over or into engagement with a tablet sample at the sample position 55 so that essentially only light that has been transmitted through the sample is passed through the aperture. The detector 60 may be mounted so that it can be moved downwardly to be more closely adjacent to the sample during measurements. Thus, reflection and transmission measurements of the same sample may be carried out, sequentially or simultaneously, without moving the sample.

Figure 3:
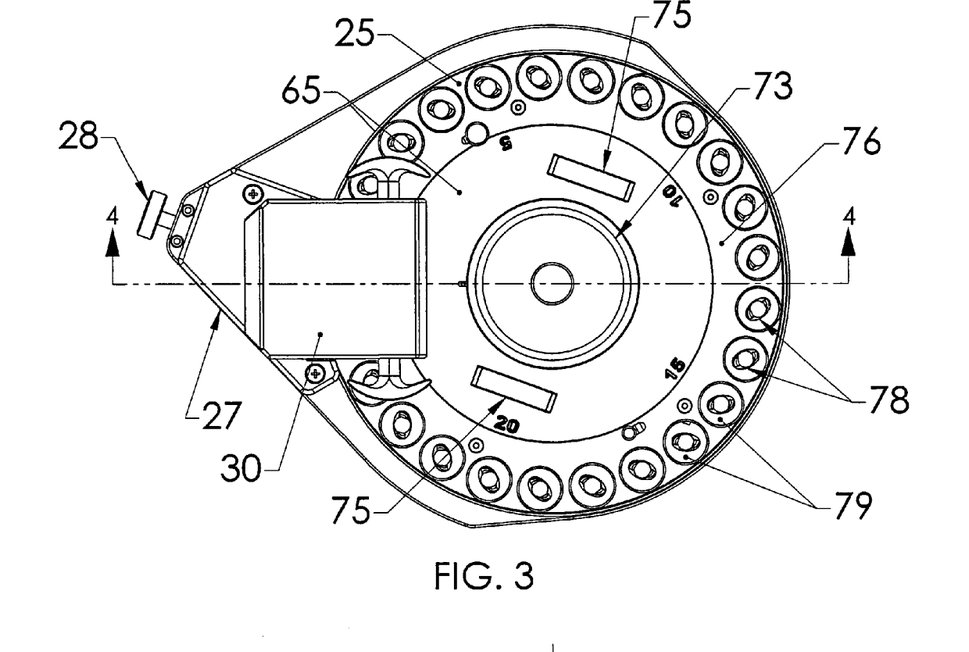
FIG. 3 is a top plan view of a tablet holding wheel system in accordance with the invention.
Figure 4:
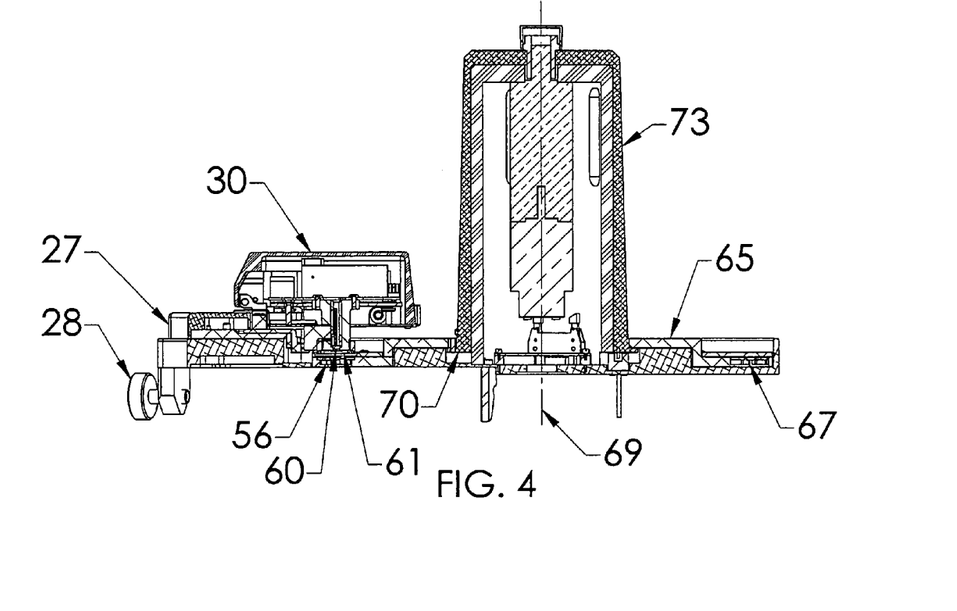
FIG. 4 is a cross-sectional view of the tablet holding wheel system of FIG. 3 taken generally along the lines 4—4 of FIG. 3.

FIG. 3 shows a top view of the tablet wheel system 25 and FIG. 4 shows a cross-section through the tablet wheel system along the lines 4—4 of FIG. 3. The tablet holding wheel 25 has a tablet wheel base 65 which has a plurality of transmission openings 67 arranged in a circular pattern around a central axis 69, with the base 65 being supported on a plate 70 that is formed as a ledge extending from a motor-driven outer housing 73, mounting the base for rotation about its central axis 69. The grippers 56 are formed adjacent to each transmission opening and are movable inwardly and outwardly over the transmission opening such that the grippers, when moved inwardly, can engage and hold a tablet in position over each transmission opening. The outer motor housing 73 centers the base 65, which is engaged to the plate 70 by a pin to drive the tablet wheel in rotation about the central axis to bring successive transmission openings into registration with the sample position 55 beneath the detector 60. As best illustrated in FIGS. 1 and 3, handles 75 are connected to the tablet wheel base 65 for convenience in transporting the tablet holding wheel, positioning it with respect to the spectrometer, and removing it when a sampling project has been completed. The tablet holding wheel also has a cover plate 76 mounted to the base 65 which has openings 78 therein that align with the transmission openings 67 in the base so that a light beam passed through a transmission opening 67 in the base will pass through an opening 78 in the cover plate. A depressed well 79 is formed about each of the openings 78, with the top edge of each well preferably chamfered, so that a movable head 62 within which the detector 60 is mounted can fit down into a well 79 to best engage a tablet held in the grippers above each transmission opening 67 during transmission measurements.

Figure 5:
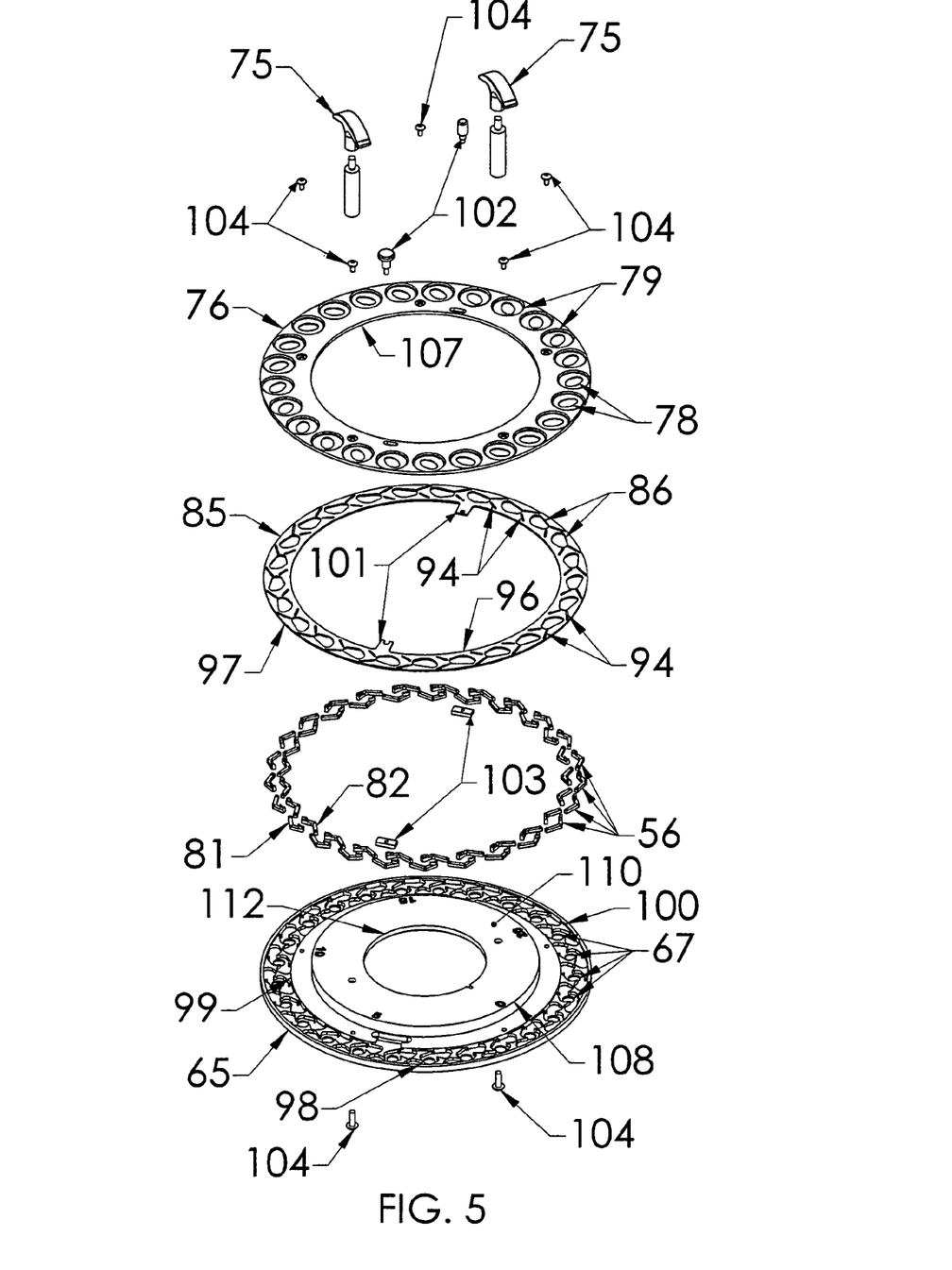
FIG. 5 is an exploded view showing the parts of the tablet holding wheel in position for assembly.
Figure 6:
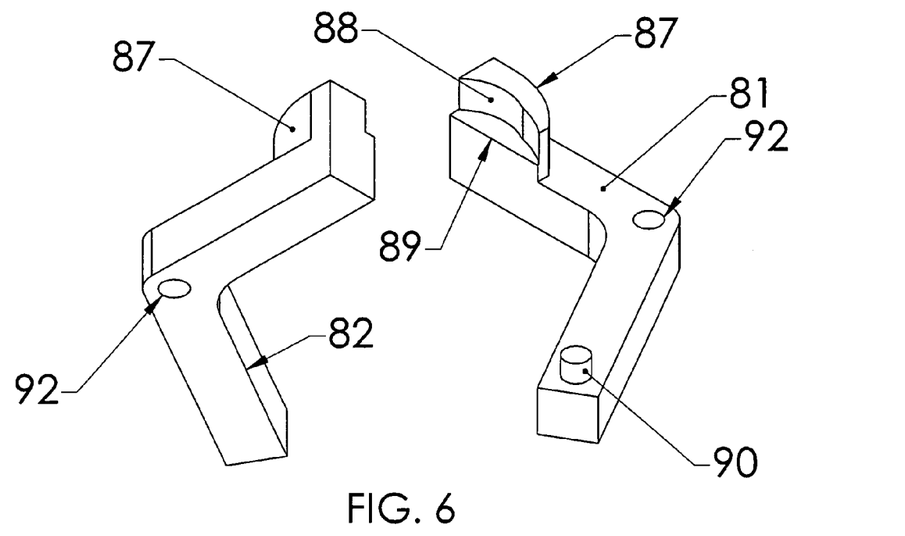
FIG. 6 is a perspective view of the gripping arms of the tablet holding wheel.

An exploded view of the tablet holding wheel 25, illustrating the parts thereof in position for assembly, is shown in FIG. 5. The grippers 56 are mounted to the base 65 adjacent to each transmission opening 67 in the base. As illustrated in FIG. 5, and described further below, each of the grippers 56 may comprise two gripping arms 81 and 82 mounted for rotation to the base about a pivot point adjacent to each transmission opening in the base. The arms 81 and 82 may be bent as shown to reduce space requirements but also may be straight, curved, etc. A cam ring 85 is then mounted over the grippers 56 and is rotatable with respect to the base about the central axis of the base in two opposite rotational directions. The cam ring 85 is operatively engaged with the grippers 56 to move the grippers outwardly in one direction of rotation of the cam ring and to move the grippers inwardly in the other direction of rotation of the cam ring so that the grippers can engage and hold tablets over the transmission openings. The grippers serve to accurately position the tablets over the transmission openings. The cam ring 85 has a plurality of openings 86 formed therein which are aligned with each of the transmission openings in the base. As illustrated in FIG. 6, the gripping arms 81 and 82 each have a gripping head 87 having an inner surface 88 shaped to engage a portion of a tablet at one end of the arm, and a cam pin 90 extending from the opposite end of the arm from the gripping head. The gripping head inner surface 88 preferably has a curved shape which extends from the arm 81 to define a ledge 89 on which a tablet can be partially supported when the gripping heads engage a tablet. The surfaces 88 may be substantially circular, elliptical, V-shaped, etc., to facilitate engagement with a tablet, but may also be flat, ribbed, etc., as well as formed of resilient material. The arms 81 and 82 are pivotally connected to the base at a central position opening 92 of the gripping arms, preferably by a pin (not shown in FIG. 6) that extends upwardly from the base and which is inserted into the opening 92 at the central position of the gripping arm, so that the gripping arm can pivot about the position of the opening 92 to bring the gripper heads 87 either closer to or further away from each other. The pin may also be formed integrally with the arm or mounted thereto, and any other pivotal connection of the arms maybe be utilized. The pins 90 are inserted into slots 94 in the cam ring 85 such that each cam pin 90 is inserted and slidable within a slot 94 in the cam ring. The slots 94 are oriented such that rotating the cam ring in one of its directions of motion drives the cam pins to rotate the gripper heads 87 inwardly, and such that the slots 94 engage the cam pins to rotate the gripping heads of the gripping arms outwardly when the cam ring is rotated in its opposite direction of rotation.

Figure 7:
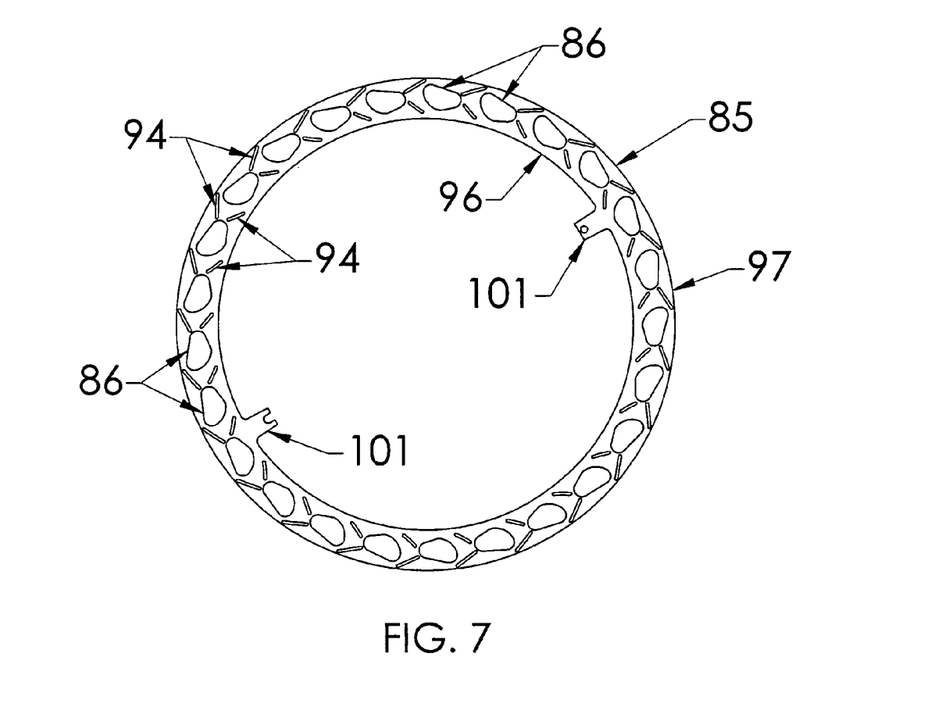
FIG. 7 is a more detailed view of the cam ring of the tablet holding wheel.
Figure 8:
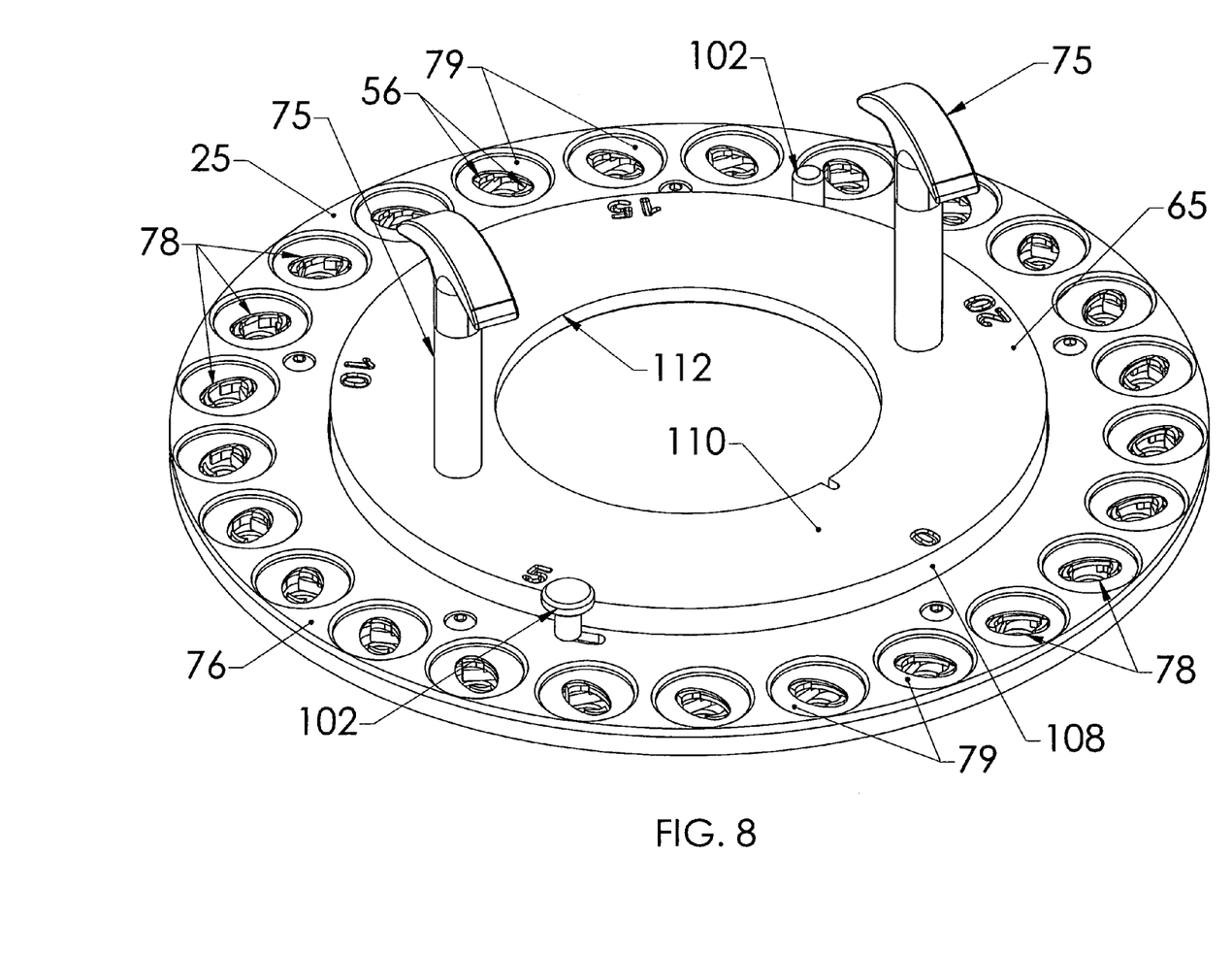
FIG. 8 is a more detailed perspective view of the assembled tablet holding wheel.

As shown in FIGS. 5 and 7, the cam ring 85 has an inner circular periphery 96 and a outer circular periphery 97, the inner circular periphery 96 of the cam ring defining a central opening of the cam ring. The base 65 has a peripheral circular channel 98 having a floor in which the transmission openings 67 are formed and upwardly raised inner and outer sidewalls 99 and 100 such that the cam ring 85 fits within the channel, with the inner periphery 96 of the cam ring adjacent to the inner sidewall 99 of the channel and the outer periphery 97 of the cam ring adjacent to the outer sidewall 100 of the channel so that the cam ring slides in rotation within the channel. Inwardly projecting elements 101 of the cam ring 85 extend through openings in the inner wall of the channel, and handles 102 are engaged therewith and threaded into blocks 103 beneath the elements 101. The handles 102 can be used by an operator to move the projecting elements 101 and the cam ring 85 connected thereto in one or the other direction of rotation of the cam ring. When the cam ring 85 is to be secured in place holding the tablets, one or both of the handles 102 can be screwed down tightly. A set of screws 104 can be threaded through corresponding openings in the cover plate 76 and base 65 to secure the cover plate to the base 65 over the cam ring 85 and the grippers 56. An inner peripheral edge 107 of the cover plate 76 engages with an outer side wall 108 of a raised central portion 110 of the base 65 to properly position the cover plate on the base. An inner circular opening 112 in the base is sized to admit and closely engage the outer surface of the drive housing 73.

A material for forming the gripper arms 81 and 82 suitable to minimize interference with the infrared transmission beam is Teflon™ (polytetrafluoroethylene). Other materials that have relatively minimal interference with the infrared beam (polypropylene, polyethylene, etc.) can also be used as well as metals, such as aluminum, with diffusing or absorbing coatings. The arms may also be formed of spring material so as to apply spring force to the tablets when engaged therewith. Because the other components of the table holding wheel generally will not be intersecting the infrared beam, various materials may be utilized for these parts. For example, the base 65 and the cover plate 76 may be formed of (e.g., black anodized) aluminum, and the cam ring 85 may be formed of, for example, a plastic such as Delrin® (polyoxymethylene).

The tablet holding wheel 25 may be formed as an integral part of the spectrometer or as an accessory which can be selectively attached to or detached from the spectrometer. When employed as an accessory for the spectrometer, the tablet holding wheel 25 is carried to the spectrometer and mounted on the top of the spectrometer so that the detector 60 is positioned over the sample position at the exit opening 59 for the beam from the spectrometer. The handles 75 are conveniently utilized to carry the tablet holding wheel to the spectrometer and place it in its proper position. The hand screw connector 28 may then be turned by the operator to screw into the housing of the sample chamber 23 to mount the tablet holding wheel securely in place in its proper position. The rotational drive motor in the housing 73 is connected to the controls of the spectrometer so that its operation can be controlled by the spectrometer. To put tablets in place on the tablet holding wheel, the operator grasps the handles 102 and uses them to move the cam ring in its direction of motion which drives the gripping heads 87 outwardly. The operator then places a tablet in one or more of the tablet holding positions in the wheel 25 between the gripping heads of the grippers. The operator then uses the handle 102 to move the cam ring in its opposite direction of rotation to cause the gripper arms to pivot the gripping heads inwardly to firmly engage the tablets to be held between the gripping heads and then tightens a handle 102 down to securely hold the tablets in position. The gripping heads are shaped so that they will engage the tablets to orient the tablets in a specified direction of orientation for nonsymmetric tablets, such as a oval tablets or gel capsules. The operator then places tablets at some or all of the other sample positions. Generally, it is more convenient for the operator to put the tablets in position while the tablet holding wheel is removed from the spectrometer and then mounting the wheel to the spectrometer. Having placed the wheel with its tablets in their proper positions, the operator then can operate the spectrometer to begin analyzing the tablets held within the tablet wheel. The spectrometer automatically advances the tablet wheel using the drive motor to bring successive tablets into the sample position, to carry out spectrographic analysis on the sample, to move the tablet wheel to the next position, and to repeat the process until all of the tablets have been analyzed. The operator may then remove the tablet wheel from the spectrometer to allow the tablets to be removed, and another set of tablet samples may then be inserted between the gripping heads the tablet wheel before it is reinstalled on the spectrometer. Because the grippers adapt to different shapes and sizes of tablets, no replacement of the tablet wheel is required to adapt to a new batch of tablets having a different shape or size than the previous batch. After all of the tablets in a particular project have been analyzed, if the spectrometer is to be utilized for other purposes than tablet analysis, the operator can lift the tablet wheel 25 by the handles 75 and move it to a convenient storage place.

It is understood that the invention is not confined to the particular embodiments set forth herein as illustrative, but embraces all such forms thereof as come within the scope of the following claims.

What is claimed is:

1. A tablet holding wheel for a spectrometer comprising:
   (a) a tablet wheel base having a plurality of transmission openings therein arranged in a circular pattern around a central axis of the base, the base rotatable about its central axis;
   (b) grippers adjacent to each of the transmission openings that are movable inwardly and outwardly over the transmission openings such that the grippers when moved inwardly can engage a tablet over each transmission opening; and
   (c) a cam ring mounted to the tablet wheel base and rotatable with respect to the base about the central axis of the base in two opposite rotational directions, the cam ring being operatively engaged with the grippers to move the grippers outwardly in one direction of rotation of the cam ring and to move the grippers inwardly in the other direction of rotation of the cam ring, whereby the grippers can engage and hold tablets over the transmission openings.

2. The tablet holding wheel of claim 1 further including a cover plate mounted to the base over the cam ring such that the cam ring slides between the cover plate and the base as the cam ring is rotated.

3. The tablet holding wheel of claim 2 wherein the cover plate has openings therein which are aligned with the transmission openings in the base so that a beam of light passed through a transmission opening in the base will pass through the opening in the cover plate, and further including a depressed well formed in the cover plate about each of the openings therein.

4. The tablet holding wheel of claim 1 wherein the grippers comprise two gripping arms mounted for rotation about a pivot point adjacent each transmission opening in the base, each arm having a gripping head shaped to engage a portion of a tablet at one end of the arm and a cam pin extending from the opposite end of the arm from the gripping head, with the arm being pivotally connected to the base at a central position of the arm between the gripping head and the cam pin, and wherein the cam ring has a plurality of openings therein that are aligned with each of the openings in the base and which enclose the gripping heads of the gripping arms to permit movement of the gripping heads inwardly and outwardly within the openings in the cam ring, and wherein the cam ring further includes slots therein for each of the cam pins of the gripping arms with each cam pin of each gripping arm inserted and slidable within a slot in the cam ring, the slots oriented such that rotation of the cam ring in one of its directions of motion drives the cam pins to rotate the gripping heads of the gripping arms inwardly and wherein the slots engage the cam pins to rotate the gripping heads of the gripping arms outwardly when the cam ring is rotated in its opposite direction of motion.

5. The tablet holding wheel of claim 4 wherein the gripping heads are formed to have a portion extending upwardly through the openings in the cam ring and above adjacent portions of each gripping arm.

6. The tablet holding wheel of claim 5 wherein the portions of the gripping heads extending above the adjacent portions of each gripping arm has a curved inwardly facing surface suited to engage a curved surface of a tablet.

7. The tablet holding wheel of claim 4 wherein the gripping arms are formed of polytetrafluoroethylene.

8. The tablet holding wheel of claim 1 wherein the cam ring has an outer and inner circular periphery, the inner circular periphery of the cam ring defining a central opening of the cam ring, wherein the base has a peripheral circular channel having a floor in which the transmission openings are formed and upwardly raised inner and outer sidewalls such that the cam ring fits within the channel with the inner periphery of the cam ring adjacent to the inner sidewall of the channel and the outer periphery of the cam ring adjacent to the outer sidewall of the channel, such that the cam ring slides in rotation within the channel, and including an inwardly projecting element of the cam ring extending through an opening in the inner sidewall of the channel and a handle engaged therewith which can be operated by an operator to move the projecting element and the cam ring connected thereto in one or the other direction of rotation of the cam ring.

9. The tablet holding wheel of claim 8 further including a cover plate mounted to the base and extending over the cam ring such that the cover plate covers the cam ring as it slides within the channel of the base, the cover plate having openings therein aligned with the openings in the cam ring and the transmission openings in the base, and having depressed wells therein around each opening in the cover plate, the cover plate having an inner periphery defining a central opening engaged with an upraised inner central wall of the base.

10. The tablet holding wheel of claim 9 wherein the openings in the cover plate are oval in shape with the sides of each opening at the shorter dimension of each opening being adjacent to and outwardly spaced from upwardly extending gripping heads of the gripping arms.

11. A tablet holding wheel for a spectrometer comprising:
(a) a tablet wheel base having a plurality of transmission openings therein arranged in a circular pattern around a central axis of the base, the base rotatable about its central axis;
(b) grippers adjacent to each of the transmission openings comprising two gripping arms mounted for rotation about a pivot point adjacent each transmission opening in the base, each arm having a gripping head shaped to engage a portion of a tablet at one end of the arm and a cam pin extending from the opposite end of the arm from the gripping head, with the arm being pivotally connected to the base at a central position of the arm between the gripping head and the cam pin;
(c) a cam ring mounted to the tablet wheel base and rotatable with respect to the base about the central axis of the base in two opposite rotational directions wherein the cam ring has a plurality of openings therein that are aligned with each of the transmission openings in the base and which enclose the gripping heads of the gripping arms to permit movement of the gripping heads inwardly and outwardly within the openings in the cam ring, and wherein the cam ring further includes slots therein for each of the cam pins of the gripping arms with each cam pin of each gripping arm inserted and slidable within a slot in the cam ring, the slots oriented such that rotation of the cam ring in one of its directions of motion drives the cam pins to rotate the gripping heads of the gripping arms inwardly and wherein the slots engage the cam pins to rotate the gripping heads of the gripping arms outwardly when the cam ring is rotated in its opposite direction of motion; and
(d) a cover plate mounted to the base over the cam ring such that the cam ring slides between the cover plate and the base as the cam ring is rotated, the cover plate having openings therein aligned with the transmission openings in the base.

12. The tablet holding wheel of claim 11 wherein the cover plate includes a depressed well formed in the cover plate about each of the openings therein.

13. The tablet holding wheel of claim 11 wherein the gripping heads are formed to have a portion extending upwardly through the openings in the cam ring and above adjacent portions of each gripping arm.

14. The tablet holding wheel of claim 13 wherein the portions of the gripping heads extending above the adjacent portions of each gripping arm has a curved inwardly facing surface suited to engage a curved surface of a tablet.

15. The tablet holding wheel of claim 11 wherein the gripping arms are formed of polytetrafluoroethylene.

16. The tablet holding wheel of claim 11 wherein the cam ring has an outer and inner circular periphery, the inner circular periphery of the cam ring defining a central opening of the cam ring, wherein the base has a peripheral circular channel having a floor in which the transmission openings are formed and upwardly raised inner and outer sidewalls such that the cam ring fits within the channel with the inner periphery of the cam ring adjacent to the inner sidewall of the channel and the outer periphery of the cam ring adjacent to the outer sidewall of the channel, such that the cam ring slides in rotation within the channel, and including an inwardly projecting element of the cam ring extending through an opening in the inner sidewall of the channel and a handle engaged therewith which can be operated by an operator to move the projecting element and the cam ring connected thereto in one or the other direction of rotation of the cam ring.

17. The tablet holding wheel of claim 11 wherein the cover plate has an inner periphery defining a central opening engaged with an upraised inner central wall of the base.

18. The tablet holding wheel of claim 11 wherein the openings in the cover plate are oval in shape with the sides of each opening at the shorter dimension of each opening being adjacent to and outwardly spaced from upwardly extending gripping heads of the gripping arms.

19. An infrared spectrometer system comprising:
(a) an infrared spectrometer which provides a modulated output beam on a beam path;
(b) optical elements transmitting the modulated output beam from the spectrometer on a beam path and providing a converging infrared beam directed toward a sample position;
(c) a reflected light infrared detector which detects infrared light from the infrared beam that is reflected from a sample at the sample position;
(d) a transmitted light infrared detector mounted adjacent to the sample position above the sample position to receive infrared light passed through a sample held in the sample position;
(e) a tablet holding wheel mounted to advance multiple tablets one at a time to the sample position, comprising:
(1) a tablet wheel base having a plurality of transmission openings therein arranged in a circular pattern around a central axis of the base, the base rotatable about its central axis;
(2) grippers adjacent to each of the transmission openings that are movable inwardly and outwardly over the transmission openings such that the grippers when moved inwardly can engage a tablet over each transmission opening; and
(3) a cam ring mounted to the tablet wheel base and rotatable with respect to the base about the central axis of the base in two opposite rotational directions, the cam ring being operatively engaged with the grippers to move the grippers outwardly in one direction of rotation of the cam ring and to move the grippers inwardly in the other direction of rotation of the cam ring whereby the grippers can engage and hold tablets over the transmission openings.

20. The spectrometer system of claim 19 further including a cover plate mounted to the base over the cam ring such that the cam ring slides between the cover plate and the base as the cam ring is rotated, the cover plate having openings therein aligned with the transmission openings in the base.

21. The spectrometer system of claim 20 wherein the cover plate further includes a depressed well formed in the cover plate about each of the openings therein.

22. The spectrometer system of claim 19 wherein the grippers comprise two gripping arms mounted for rotation about a pivot point adjacent each transmission opening in the base, each arm having a gripping head shaped to engage a portion of a tablet at one end of the arm and a cam pin extending from the opposite end of the arm from the gripping head, with the arm being pivotally connected to the base at a central position of the arm between the gripping head and the cam pin, and wherein the cam ring has a plurality of openings therein that are aligned with each of the openings in the base and which enclose the gripping heads of the gripping arms to permit movement of the gripping heads inwardly and outwardly within the openings in the cam ring, and wherein the cam ring further includes slots therein for each of the cam pins of the gripping arms with each cam pin of each gripping arm inserted and slidable within a slot in the cam ring, the slots oriented such that rotation of the cam ring in one of its directions of motion drives the cam pins to rotate the gripping heads of the gripping arms inwardly and wherein the slots engage the cam pins to rotate the gripping heads of the gripping arms outwardly when the cam ring is rotated in its opposite direction of rotation.

23. The spectrometer system of claim 22 wherein the gripping heads are formed to have a portion extending upwardly through the openings in the cam ring and above adjacent portions of each gripping arm.

24. The spectrometer system of claim 23 wherein the portions of the gripping heads extending above the adjacent portions of each gripping arm has a curved inwardly facing surface suited to engage a curved surface of a tablet.

25. The spectrometer system of claim 22 wherein the gripping arms are formed of polytetrafluoroethylene.

26. The spectrometer system of claim 22 wherein the cam ring has an outer and inner circular periphery, the inner circular periphery of the cam ring defining a central opening of the cam ring, wherein the base has a peripheral circular channel having a floor in which the transmission openings are formed and upwardly raised inner and outer sidewalls such that the cam ring fits within the channel with the inner periphery of the cam ring adjacent to the inner sidewall of the channel and the outer periphery of the cam ring adjacent to the outer sidewall of the channel, such that the cam ring slides in rotation within the channel, and including an inwardly projecting element of the cam ring extending through an opening in the inner sidewall of the channel and a handle engaged therewith which can be operated by an operator to move the projecting element and the cam ring connected thereto in one or the other direction of rotation of the cam ring.

27. The spectrometer system of claim 26 further including a cover plate mounted to the base and extending over the cam ring such that the cover plate covers the cam ring as it slides within the channel of the base, the cover plate having openings therein aligned with the openings in the cam ring and the transmission openings in the base, and having depressed wells therein around each opening in the cover plate, the cover plate having an inner periphery defining a central opening engaged with an upraised inner central wall of the base.

28. The spectrometer system of claim 27 wherein the openings in the cover plate are oval in shape with the sides of each opening at the shorter dimension of each opening being adjacent to and outwardly spaced from upwardly extending gripping heads of the gripping arms.

29. The spectrometer system of claim 19 wherein the reflected light detector includes an integrating sphere having a hollow spherical interior, an inlet opening in the integrating sphere which receives the converging beam on the beam path, an outlet opening in the integrating sphere through which the beam passes to the sample position, and a detector mounted to the integrating sphere to receive infrared radiation reflected from the interior surfaces of the integrating sphere, the interior surfaces of the integrating sphere formed to provide diffuse reflection.

* * * * *